US010111731B2

(12) United States Patent
Sommer et al.

(10) Patent No.: US 10,111,731 B2
(45) Date of Patent: Oct. 30, 2018

(54) SELF-LIGATING BRACKET

(71) Applicant: American Orthodontics Corporation, Sheboygan, WI (US)

(72) Inventors: Jay S. Sommer, Howards Grove, WI (US); Eric W. Nimmer, Plymouth, WI (US)

(73) Assignee: AMERICAN ORTHODONTICS CORPORATION, Sheboygan, WI (US)

( * ) Notice: Subject to any disclaimer, the term of this patent is extended or adjusted under 35 U.S.C. 154(b) by 126 days.

(21) Appl. No.: 14/938,515

(22) Filed: Nov. 11, 2015

(65) Prior Publication Data

US 2016/0135929 A1 May 19, 2016

Related U.S. Application Data

(60) Provisional application No. 62/081,387, filed on Nov. 18, 2014.

(51) Int. Cl.
*A61C 7/28* (2006.01)
*A61C 7/14* (2006.01)

(52) U.S. Cl.
CPC .............. *A61C 7/287* (2013.01); *A61C 7/146* (2013.01)

(58) Field of Classification Search
CPC ................................ A61C 7/287; A61C 7/146
See application file for complete search history.

(56) References Cited

U.S. PATENT DOCUMENTS

| 2,549,528 | A | 4/1951 | Russell |
| 2,671,964 | A | 3/1954 | Russel et al. |
| 3,131,474 | A | 5/1964 | Johnson |
| 4,197,642 | A | 4/1980 | Wallshein |
| 4,248,588 | A | 2/1981 | Hanson |
| 4,419,078 | A | 12/1983 | Pletcher |
| 4,492,573 | A | 1/1985 | Hanson |
| 5,094,614 | A | 3/1992 | Wildman |

(Continued)

FOREIGN PATENT DOCUMENTS

| DE | 4407100 A1 | 9/1995 |
| DE | 102009029834 | 12/2010 |

(Continued)

OTHER PUBLICATIONS

Agility Self-Ligating Passive System by Orthodontic Design and Production, Inc., acquired Mar. 10, 2014.

*Primary Examiner* — Cris L Rodriguez
*Assistant Examiner* — Hao D Mai
(74) *Attorney, Agent, or Firm* — Andrus Intellectual Property Law, LLP

(57) ABSTRACT

A self-ligating bracket include a bracket body with an arch wire slot. A mesial recess is located at a mesial side of the bracket body and extends into the bracket body from the arch wire slot. A distal recess is located at a distal side of the bracket body and extends into the bracket body from the arch wire slot. A central ridge defines a ridge surface separated from the lateral ledges respectively by mesial and distal walls. A clip includes a first arm and a second arm connected by a U-shaped portion. The first arm terminates in a mesial arm, a distal arm, and a middle arm. The clip is moveable between an open position in which the arch wire slot is accessible and a closed position in which the arch wire slot is occluded.

21 Claims, 15 Drawing Sheets

(56) References Cited

U.S. PATENT DOCUMENTS

| | | |
|---|---|---|
| 5,275,557 A | 1/1994 | Damon |
| 5,322,435 A | 6/1994 | Pletcher |
| 5,429,500 A | 7/1995 | Damon |
| 5,439,378 A | 8/1995 | Damon |
| 5,466,151 A | 11/1995 | Damon |
| 5,474,445 A | 12/1995 | Voudouris |
| 5,474,446 A | 12/1995 | Wildman et al. |
| 5,562,444 A | 10/1996 | Heiser et al. |
| 5,613,850 A | 3/1997 | Wildman et al. |
| 5,630,715 A | 5/1997 | Voudouris |
| 5,711,666 A | 1/1998 | Hanson |
| 5,800,162 A | 9/1998 | Shimodaira et al. |
| 5,857,849 A | 1/1999 | Kurz |
| 5,857,850 A | 1/1999 | Voudouris |
| 5,906,486 A | 5/1999 | Hanson |
| 5,908,293 A | 6/1999 | Voudouris |
| 5,913,680 A | 6/1999 | Voudouris |
| 6,071,118 A | 6/2000 | Damon |
| 6,071,119 A | 6/2000 | Christoff |
| 6,168,428 B1 | 1/2001 | Voudouris |
| 6,247,923 B1 | 6/2001 | Vashi |
| 6,257,883 B1 | 7/2001 | Voudouris |
| 6,325,622 B1 | 12/2001 | Kelly et al. |
| 6,368,105 B1 | 4/2002 | Voudouris |
| 6,464,495 B1 | 10/2002 | Voudouris |
| 6,554,612 B2 | 4/2003 | Georgakis et al. |
| 6,632,088 B2 | 10/2003 | Voudouris |
| 6,659,766 B2 | 12/2003 | Abels et al. |
| 6,733,286 B2 | 5/2004 | Abels et al. |
| 6,776,613 B2 | 8/2004 | Orikasa |
| 6,843,651 B2 | 1/2005 | Orikasa |
| 6,939,133 B2 | 9/2005 | Voudouris |
| 7,104,791 B2 | 9/2006 | Hanson |
| 7,214,057 B2 | 5/2007 | Voudouris |
| 7,247,019 B2 | 7/2007 | Abels |
| 7,255,557 B2 | 8/2007 | Forster |
| 7,267,545 B2 | 9/2007 | Oda |
| 7,335,020 B2 | 2/2008 | Castner et al. |
| 7,416,408 B2 | 8/2008 | Farzin-Nia et al. |
| 7,419,375 B2 | 9/2008 | Farzin-Nia et al. |
| 7,442,039 B2 | 10/2008 | Opin |
| 7,481,651 B2 | 1/2009 | Sernetz et al. |
| 7,611,353 B2 | 11/2009 | Sommer |
| 7,621,743 B2 | 11/2009 | Bathen et al. |
| 7,704,072 B2 | 4/2010 | Damon |
| 7,785,101 B2 | 8/2010 | Forster |
| 7,845,939 B2 | 12/2010 | Minium |
| 7,909,603 B2 | 3/2011 | Oda |
| 7,963,767 B2 | 6/2011 | Lewis et al. |
| 8,029,276 B1 | 10/2011 | Lokar |
| 8,033,824 B2 | 10/2011 | Oda et al. |
| 8,038,438 B2 | 10/2011 | Ruiz Diaz et al. |
| 8,113,827 B2 | 2/2012 | Farzin-Nia et al. |
| 8,246,348 B2 | 8/2012 | Heiser |
| 8,246,349 B2 | 8/2012 | Scommegna et al. |
| 8,251,696 B2 | 8/2012 | Rodriguez et al. |
| 8,282,392 B2 | 10/2012 | Hilliard |
| 8,297,970 B2 | 10/2012 | Kanomi et al. |
| 8,393,896 B2 | 3/2013 | Oda |
| 8,414,292 B2 | 4/2013 | Lopes |
| 8,568,138 B2 | 10/2013 | Farzin-Nia et al. |
| 8,585,398 B2 | 11/2013 | Yeh et al. |
| 8,636,507 B2 * | 1/2014 | Voudouris ............... A61C 7/287 433/10 |
| 8,726,510 B2 | 5/2014 | Voudouris |
| D710,998 S | 8/2014 | Voudouris |
| 8,932,053 B2 | 1/2015 | Curiel et al. |
| 8,944,811 B2 | 2/2015 | Curiel et al. |
| 2002/0187452 A1 | 12/2002 | Abels et al. |
| 2003/0039938 A1 * | 2/2003 | Orikasa ................. A61C 7/287 433/11 |
| 2004/0166459 A1 | 8/2004 | Voudouris |
| 2004/0170942 A1 | 9/2004 | Heiser |
| 2004/0175667 A1 | 9/2004 | Abels et al. |
| 2004/0175669 A1 | 9/2004 | Abels et al. |
| 2004/0175699 A1 | 9/2004 | Fiszman |
| 2005/0239012 A1 | 10/2005 | Bathen et al. |
| 2005/0244772 A1 | 11/2005 | Abels et al. |
| 2007/0072143 A1 | 3/2007 | Sommer |
| 2007/0166658 A1 | 7/2007 | Voudouris |
| 2007/0178422 A1 | 8/2007 | Voudouris |
| 2009/0004617 A1 | 1/2009 | Oda et al. |
| 2009/0325119 A1 | 12/2009 | Sierk |
| 2010/0105000 A1 | 4/2010 | Scommegna et al. |
| 2010/0261131 A1 | 10/2010 | Ruiz-Vela et al. |
| 2010/0311004 A1 | 12/2010 | Voudouris |
| 2011/0076633 A1 | 3/2011 | Bryant et al. |
| 2011/0136071 A1 | 6/2011 | Levens |
| 2012/0028206 A1 | 2/2012 | Lopes |
| 2013/0125398 A1 | 5/2013 | Curiel et al. |
| 2013/0171579 A1 * | 7/2013 | Orikasa ................... A61C 7/02 433/10 |
| 2013/0196279 A1 | 8/2013 | Curiel et al. |
| 2013/0260329 A1 | 10/2013 | Voudouris |
| 2013/0337397 A1 | 12/2013 | Curiel et al. |
| 2013/0337399 A1 | 12/2013 | Curiel et al. |
| 2014/0011154 A1 | 1/2014 | Curiel et al. |
| 2014/0023981 A1 | 1/2014 | Voudouris |
| 2014/0134563 A1 | 5/2014 | Voudouris |
| 2014/0199648 A1 | 7/2014 | Lopes |
| 2014/0212828 A1 | 7/2014 | Falcone et al. |
| 2014/0272750 A1 | 9/2014 | Lai |
| 2014/0272753 A1 | 9/2014 | Sommer et al. |
| 2014/0308622 A1 | 10/2014 | Voudouris |
| 2015/0125804 A1 | 5/2015 | D'Amico Neto |
| 2015/0216629 A1 | 8/2015 | Voudouris |
| 2015/0265377 A1 | 9/2015 | Wu et al. |

FOREIGN PATENT DOCUMENTS

| | | |
|---|---|---|
| EP | 0161831 B1 | 3/1996 |
| EP | 1234549 A1 | 8/2002 |
| EP | 1287789 A2 | 3/2003 |
| EP | 2644150 | 10/2013 |
| FR | 2922753 B1 | 12/2010 |
| WO | 1998020805 A1 | 5/1998 |
| WO | 2008044912 A1 | 4/2008 |
| WO | 2010028276 A1 | 3/2010 |
| WO | 2010103178 A1 | 9/2010 |
| WO | 2006094403 A1 | 9/2016 |

* cited by examiner

SELF-LIGATING BRACKET

CROSS-REFERENCE TO RELATED APPLICATION

The present application claims priority of U.S. Provisional Patent Application No. 62/081,387, filed on Nov. 18, 2014, the content of which is hereby incorporated herein by reference in its entirety.

BACKGROUND

The present disclosure is related to the field of orthodontics. More specifically, the present disclosure relates to self-ligating brackets.

Orthodontic treatment often includes at least a combination of an arch wire and brackets and/or buccal tubes that are used to secure the arch wire to the teeth of the patient. The arch wire is made of a resilient material that, if bent or deformed, will return to its previous shape. Dental malocclusions are treated by securing the arch wire to the patient's teeth which are brought into a post-treatment alignment as the arch wire returns to its original shape.

Traditionally, brackets are secured to the tooth of a patient and the brackets have an arch wire slot within which the arch wire is received. Elastomeric ligatures secure the arch wire within the arch wire slot of the bracket. Self-ligating brackets eliminate the need for separate elastomeric ligatures by mechanically securing the arch wire to the bracket.

BRIEF DISCLOSURE

An exemplary embodiment of a self-ligating bracket includes a bracket body with an arch wire slot defined therethrough in a mesial-distal dimension. The bracket body includes a mesial recess having a first lateral ledge located at a mesial side of the bracket body and extending into the bracket body from the arch wire slot. The bracket body includes a distal recess having a section lateral ledge located at a distal side of the bracket body and extending into the bracket body from the arch wire slot. The bracket body further includes a central ridge defining a ridge surface. The ridge surface is separated from the lateral ledges respectively by mesial and distal walls. A clip includes a first arm and a second arm. The first arm and the second arm are connected by a U-shaped portion. The first arm terminates in a mesial arm, a distal arm, and a middle arm between the mesial arm and the distal arm. The clip is moveable between and open position wherein the arch wire slot is accessible and a closed position wherein the arch wire slot is occluded by at least a portion of the mesial arm, the distal arm, and the middle arm. In the closed position, the mesial arm engages the first lateral edge in the mesial recess, the distal arm engages the second lateral ledge in the distal recess, and the middle arm engages the ridge surface.

A further exemplary embodiment of a self-ligating bracket includes a bracket body with an arch wire slot defined therethrough in a mesial-distal dimension. The bracket body includes a distal gingival tie wing and a mesial gingival tie wing which extend gingivally of the bracket body and are respectively located at mesial and distal sides of the bracket body. a mesial recess having a first lateral ledge and a first ceiling is defined into the mesial gingival tie wing from the arch wire slot. A distal recess having a second lateral ledge and a second ceiling is defined into the distal gingival tie wing from the arch wire slot. A cut out between the gingival tie wings defines a central ridge with a ridge surface. The ridge surface is separated from the lateral ledges respectively by mesial and distal walls. A clip includes a labial arm and a lingual arm. The labial arm and the lingual arm at connected by a U-shaped portion. The labial arm terminates in a mesial arm, a distal arm, and a middle arm between the mesial arm and the distal arm. The clip is moveable between an open position wherein the arch wire slot is accessible and a closed position wherein the arch wire slot is occluded by at least a portion of the mesial arm, the distal arm, and the middle arm. The clip is adapted such that when in the closed position, the mesial arm engages the first lateral ledge in the mesial recess, the distal arm engages the second lateral ledge in the distal recess, and the middle arm engages the ridge surface.

An exemplary embodiment of an orthodontic treatment system includes a plurality of self-ligating brackets. Each self-ligating bracket of the plurality includes a bracket body with an arch wire slot defined therethrough in a mesial-distal dimension. A mesial recess having a first lateral ledge is located at a mesial side of the bracket body and extends into the bracket body from the arch wire slot. A distal recess having a second lateral ledge is located at a distal side of the bracket body and extends into the bracket body from the arch wire slot. A central ridge defines a ridge surface. The ridge surface is separated from the lateral ledges respectively by a mesial wall and a distal wall.

A clip includes an upper arm and a lower arm. The upper arm and the lower arm are connected by a U-shaped portion. The upper arm terminates in a mesial arm, a distal arm, and a middle arm between the mesial arm and the distal arm. The clip is movable between an open position and a closed position. The clip is adapted such that when in the closed position, the mesial arm engages the first lateral ledge in the mesial recess, the distal arm engages the second lateral ledge in the distal recess, and the middle arm engages the ridge surface. An arch wire is positioned within the arch wire slot of each of the plurality of self-ligating brackets. While the clips of the self-ligating brackets are in the open position, the arch wire slots are accessible for placement in removal of the arch wire. When the clips of the self-ligating brackets are in the closed position, the arch wire is retained within the arch wire slots of each of the self-ligating brackets.

DETAILED DISCLOSURE

Exemplary embodiments of self-ligating bracket assemblies are disclosed herein. FIGS. 1-7 depict a first exemplary embodiment of a self-ligating bracket. FIGS. 8-12 depict a second exemplary embodiment of a self-ligating bracket in the form of a convertible buccal tube. FIGS. 11-14 depict a third exemplary embodiment of a self-ligating bracket in the form of a convertible double buccal tube. It is understood that the three embodiments depicted and described in further detail herein are merely exemplary embodiments and that the features and arrangements as disclosed herein may be arranged in alternative manners while remaining within and enabled by the present disclosure.

Orientational terms such as, but not limited to, mesial, distal, occlusal, gingival, labial, and lingual are used herein. It is recognized that these terms may be dependent upon an orientation of embodiments of the bracket in use within the mouth of a patient. Unless otherwise stated, the descriptions herein generally refer to use in a vestibular bracket placement technique. A person of ordinary skill in the art will recognize that embodiments as disclosed herein may also be used in a lingual technique and brackets may be oriented in other manners from the description found herein while remaining within the scope of the present disclosure.

Figure 1:
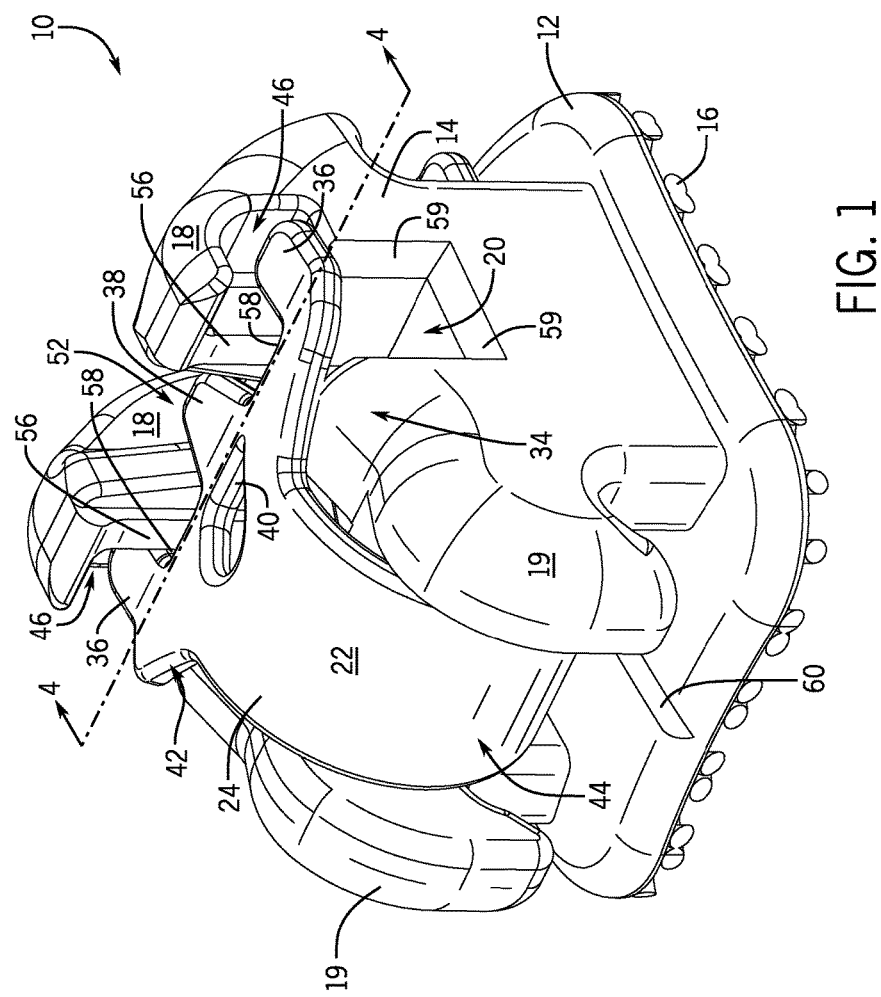
FIG. 1 is a front perspective view of an exemplary embodiment of a self-ligating bracket.
Figure 2:
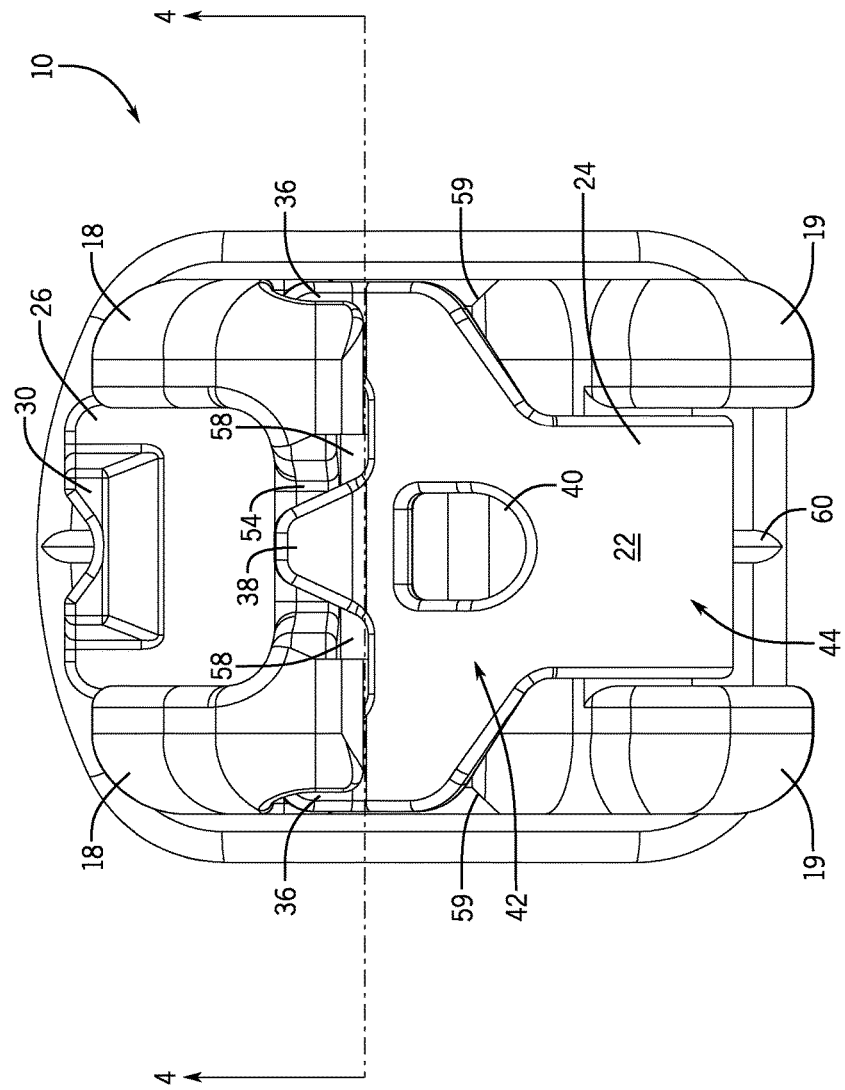
FIG. 2 is a top view of the exemplary embodiment of the self-ligating bracket.
Figure 3:
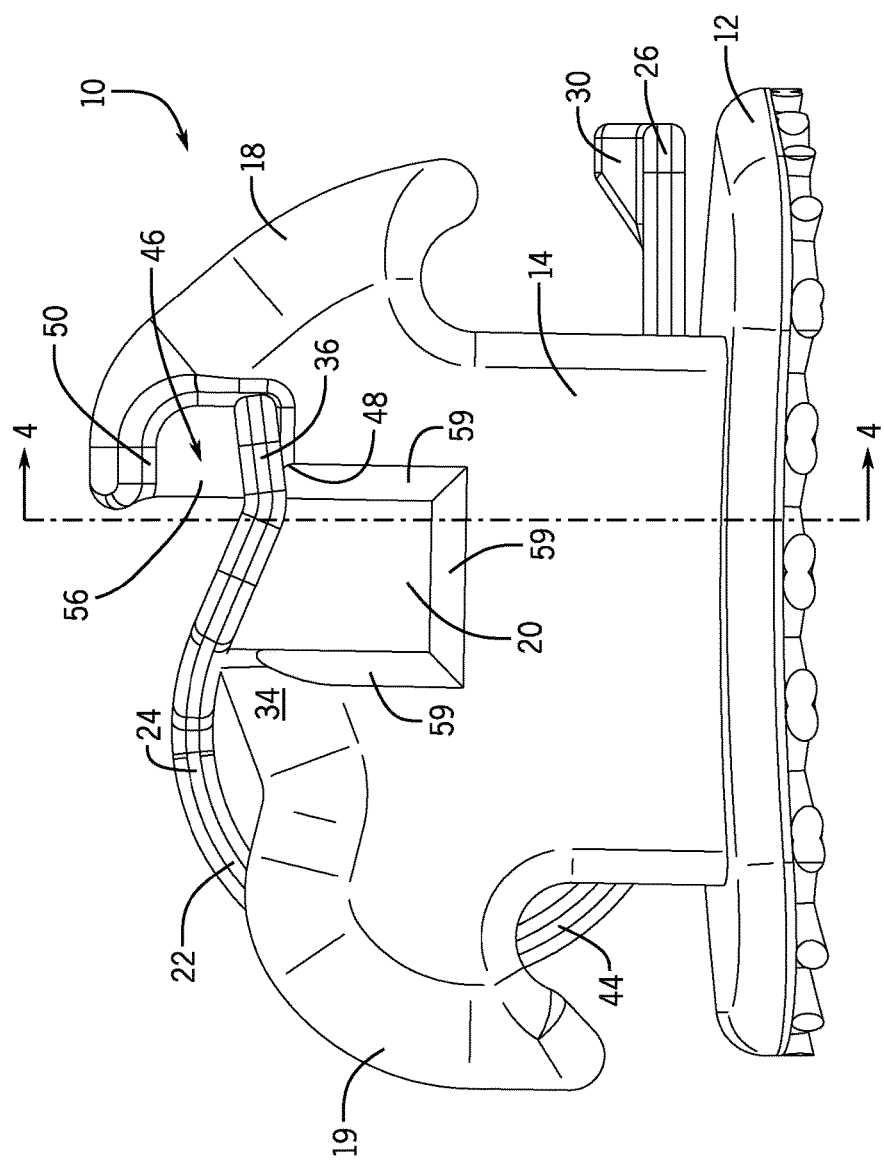
FIG. 3 is a side view of the exemplary embodiment of the self-ligating bracket.

FIG. 1 is a front perceptive view of an exemplary embodiment of a self-ligating bracket 10. The self-ligating bracket 10 is configured exemplarily for use in connection with a premolar, canine, or incisor, although this is not intended to be limiting and the potential uses of such an embodiment. Furthermore, exemplary embodiments of the self-ligating bracket 10 may be used in either lingual or vestibular applications. The self-ligating bracket 10 generally includes a base 12 and a bracket body 14 secured to the base 12. In embodiments, the bracket body 14 may be welded to the base 12, while in other embodiments, the bracket body 14 and base 12 may be integral components. In embodiments, a surface treatment 16 may be secured to the underside of the base to be secured to the patient's tooth. The surface treatment 16 depicted in FIG. 1 includes a wire mesh although it will be recognized that in alternative embodiments other forms of surface treatment including etched and textured applications may by used additionally or instead of the wire mesh. In exemplary embodiments, the surface treatment 16 provides additional surface area to facilitate the bonding of the base 12 to the tooth of a patient.

The bracket body 14 of the self-ligating bracket 10 further includes at least one tie wing. In the exemplary embodiment of the self-ligating bracket 10 depicted in FIG. 1, the self-ligating bracket 10 includes four tie wings including gingival tie wings 18 and occlusal tie wings 19. The tie wings 18, 19 are generally oriented at the corners of the bracket body 14. Tie wings 18 generally provide the function of facilitating ligation of the arch wire. While in embodiments disclosed herein, the brackets are self-ligating meaning that separate ligatures are not necessary, in some uses an orthodontist may additionally use one or more tie wings in conjunction with elastomeric ligatures to provide additional ligation, tie offs, or cross tie offs in conjunction with the self-ligating bracket 10.

Figure 15:
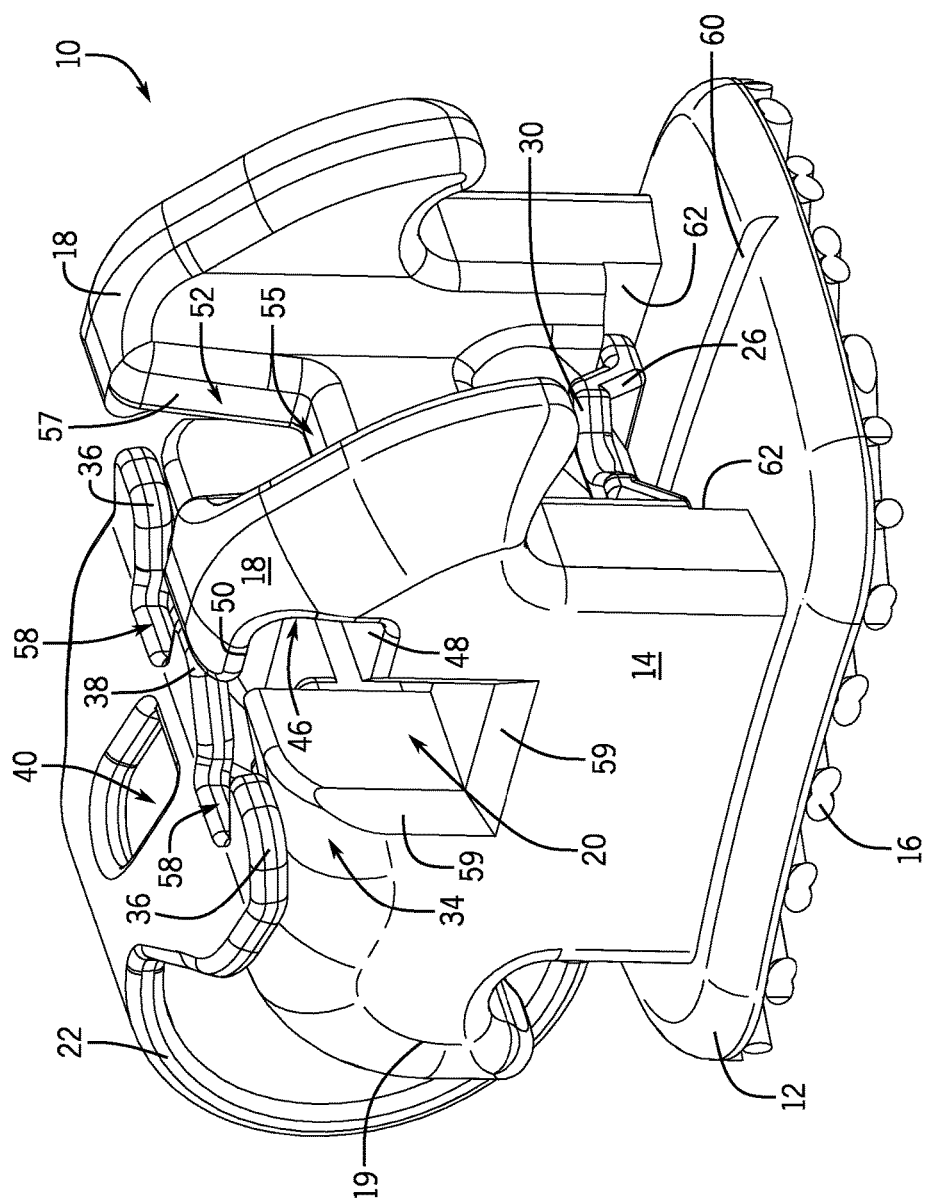
FIG. 15 is a perspective view of the exemplary embodiment of the self-ligating bracket of FIG. 1 in an open position.

The bracket body 14 further includes an arch wire slot 20 which is exemplarily arranged to receive an orthodontic arch wire (not depicted) within the arch wire slot 20. An orthodontic assembly includes a plurality of brackets secured to the teeth of a patient and connected by an arch wire. The arch wire is exemplarily constructed of a memory metal (e.g. nickel-titanium) such that the arch wire seeks to return to an original shape, thereby imparting a corrective force upon the dentition of the patient. In other embodiments, the arch wire may be constructed of other materials including, but not limited to stainless steel. It is understood that in embodiments, the arch wire slot 20 may be angled and oriented through the bracket body 14 such as to create a self-ligating bracket 10 that will impart various corrective tilt, tip, and/or torque forces on individual teeth. The self-ligating bracket 10, in use with an arch wire may impact other rotative intrusion/extrusion, or labial/vestibular movement forces on a tooth or teeth of a patient. In a self-ligating bracket 10, a clip 22 is moveably secured to the bracket body 14 between a position wherein the arch wire slot 20 is open and able to receive an arch wire therein, and another position in which the arch wire slot 20 is occluded and movement of the arch wire is constrained. FIG. 1 exemplarily depicts the self-ligating bracket 10 in a position wherein the clip 22 occludes the arch wire slot 20. FIG. 15 exemplarily depicts the self-ligating bracket 10 in a configuration wherein the clip 22 is in an open position, permitting access to the arch wire slot 20.

In embodiments, the clip 22 is constructed of a resiliently deformable material, exemplarily a nickel titanium alloy, although it is recognized that this is merely exemplary and alternative embodiments may use clips constructed of other materials.

The clip 22 is generally U-shaped with an upper arm 24 and a lower arm 26. The upper arm, as described in further detail herein includes a transition portion 42 and lateral arms 36 and middle arm 38. The lateral arms 36 and middle arm 38 are separated by cut outs 58. The lower arm 26 translates within a gap 28 that extends between the bracket body 14 and the base 12. The lower arm 26 includes a ridge 30 that extends from an end of the lower arm 26. The ridge 30 exemplarily engages a ridge stop 32 of the bracket body 14. Engagement of the ridge stop 32 and the ridge 30 defines a fully opened position of the self-ligating bracket. In such a position, the upper arm 24 of the clip 22 flexibly moves about a shoulder 34 of the bracket body 14. In the open position, the upper arm 24 is resiliently deformed, and in particular the position of lateral arms 36 and middle arm 38 of the upper arm 24 relative to the lower arm 26, which alternatively engage the shoulder 34 when the clip 22 is in the open position and help to occlude the arch wire slot 20 when the clip 22 is in the closed position.

The clip 22 further includes a cut out 40 which promotes engagement of the tip of an orthodontic tool (not depicted), exemplarily by an orthodontist to move the clip 22 between the open and closed configuration. It is to be recognized that in alternative embodiments, the cut out 40 may instead be a detent or other specialized feature that promotes engagement with an orthodontic tool.

As will be described in further detail herein, the upper arm 24 of the clip 22 includes a transition portion 42 wherein the upper arm 24 widens in the mesial-distal direction from U-shaped portion 44 which connects the upper arm 24 and the lower arm 26 and gives the clip 22 its generally U-shaped configuration. The transition portion 42 widens in the mesial-distal direction to the lateral arms 36 and middle arm 38, wherein the lateral arms 36 are generally spaced apart such as to extend between the entire widths of the bracket body 14 and arch wire slot 20 in the mesial-distal direction. Thus, in an embodiment, the mesial side of a mesial lateral arm is coextensive with the mesial side of the bracket body 14 and the mesial end of the arch wire slot 20. Similarly, the distal side of a distal lateral arm is coextensive with the distal side of the bracket body 14 and the distal end of the arch wire slot 20. In doing so, the lateral arms 36 secure the arch wire (not depicted) at the respective mesial and distal edges of the arch wire slot 20 which improves retention of the arch wire within the arch wire slot 20. When the clip 22 is in the closed position the transition portion 42 and portions of the lateral arms 36 and middle arm 38 occlude the arch wire slot 20.

In the exemplary embodiment of the self-ligating bracket 10, recesses 46 extend into the gingival tie wings 18 and in operation of the self-ligating bracket 10 respectively receive the lateral arms 36 when the clip 22 is in the closed configuration. Each recess 46 exemplarily extends between a lateral ledge 48 defined into the tie wing 18 and a ceiling 50 defined into the tie wing 18. In an exemplary embodiment, a mesial recess 46 is open both occlusally to the arch wire slot 20 and mesially through the body 14 of the bracket 10. Similarly, a distal recess 46 is open both occlusally to the arch wire slot 20 and distally through the body 14 of the bracket 10.

The lateral ledge 48 exemplarily defines the position of the lateral arm 36 when the clip 22 is in the closed configuration. In an embodiment, the lateral ledges 48 are positioned relative to the rest of the bracket body 14 and the clip 22 such that engagement of the lateral ledges 48 with the lateral arms 36 of the clip place the clip 22 in tension. Exemplarily, this may occur by the engagement of the lateral arms 36 with the lateral ledges 48 to prevent the clip 22 from fully returning to a relaxed or unbiased state. In other embodiments, the ledges 48 and the bracket body 14 and clip 22 are dimensioned such that when the clip 22 is in the closed position the clip 22 is in a relaxed or nearly relaxed state. The ceiling 50 exemplarily defines an upper bound of movement of the lateral arm 36 away from the arch wire slot 20 exemplarily to accommodate momentary shocks or forces applied on the clip 22 by arch wire (not depicted) during orthodontic treatment. This exemplary range of movement between the lateral ledge 48 and the ceiling 50 facilitates retention of the arch wire within the arch wire slot 20 while generally maintaining the arch wire in a desired position within the arch wire slot 20.

A cut out 52 is located between the tie wings 18. The cut out 52 is exemplarily defined in part by cut out walls 51 on the mesial and distal sides of the cut out 52 and a cut out floor 53. The cut out walls 51 extend through the gingival tie wings 18 from the arch wire slot 20. The cut out floor 53 extends below (e.g. lingually) the bottom of the arch wire slot 20. A central ridge 54 is located within the cut out 52 extending between the tie wings 18. The central ridge 54 defines a ridge surface 55 which is engaged by the middle arm 38 of the clip 22 when the clip 22 is in the closed position. The central ridge 54 may include ridge extensions 57 on the mesial and distal sides of the central ridge 54. The ridge extensions 57 extend between the central ridge 54 and the gingival tie wings 18 and exemplarily slope towards each other in the distal-mesial direction until the ridge surface 55 of the central ridge. The sloped ridge extensions 57 can help to direct the middle arm 38 into engagement with the ridge surface 55. As described above with respect to the lateral ledges, the central ridge 54 and ridge surface 55 may be dimensioned so that the middle arm 38 and clip 22 resiliently or positively engages the central ridge 54 when the clip 22 is in the closed position.

Figure 4:
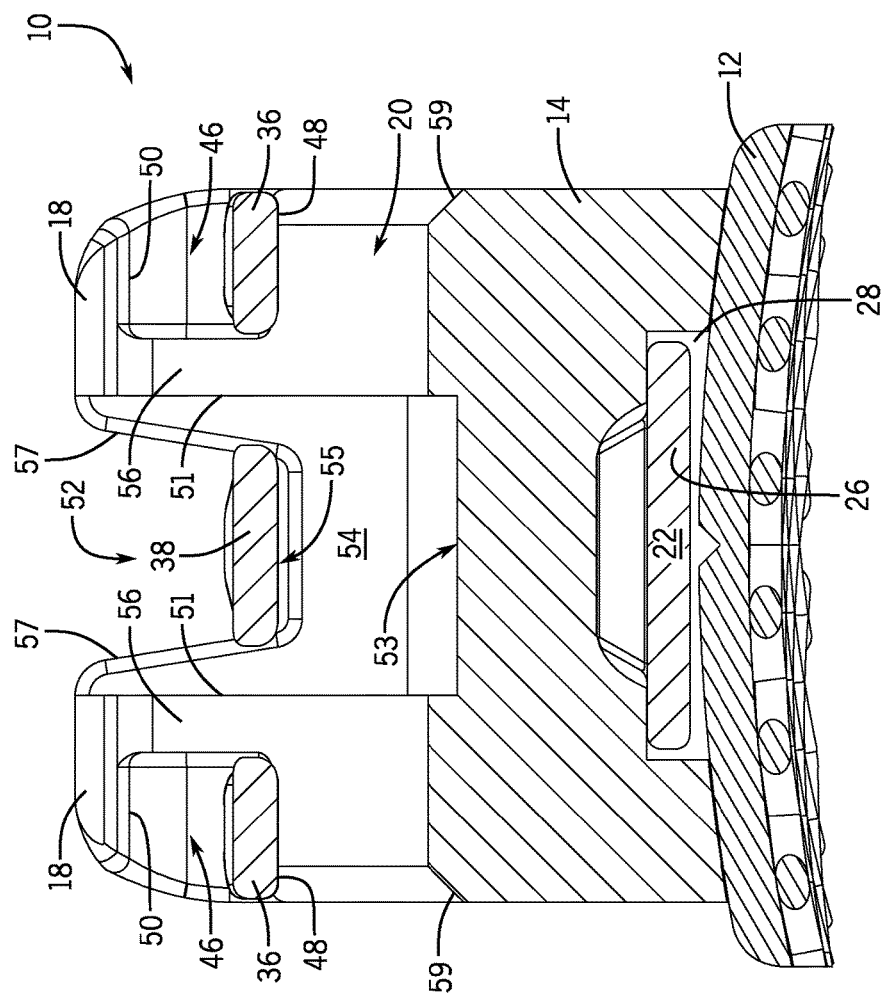
FIG. 4 is a front sectional view taken along line 4-4 of FIGS. 1-3.

As best depicted in FIG. 4, an exemplary embodiment of the cut out 52, including the cut out floor 53 extends beyond portions of the arch wire slot 20, such that a distance across the arch wire slot 20 in a central region is greater both in a gingival-occlusal dimension and/or in a labial-lingual dimension than that defined at the ends of the arch wire slot 20. The mesial and distal ends of the arch wire slot 20 may further include chamfers 59. The chamfers 59 at the mesial and distal ends of the arch wire slot 20 and the cut out 52 in the central portion of the arch wire slot 20 provide for a degree flexion of the arch wire within the arch wire slot 20 while maintaining the arch wire secure within the bracket at the mesial and distal ends of the arch wire slot 20. In embodiments this may act as a shock absorber in additional to the defined degree of travel of the lateral arms 36 to retain the arch wire within the arch wire slot 20.

In embodiments, when the clip 22 is in the closed position, occluding the arch wire slot 20 with at least some of the transition portion 42, lateral arms 36, and middle arm 38, the mesial arm and distal arm, as the lateral arms, help to secure the arch wire within the arch wire slot 20 at the respective mesial and distal ends of the arch wire slot 20. The application of an active or passive retention force, as described in further detail herein, against the arch wire at the mesial and distal ends of the arch wire slot 20 promotes improved retention of the arch wire. In an embodiment, the middle arm 38, extending between the lateral arms 36, blocks the space between the lateral arms. The inventors have found that without the middle arm 38, as the clip 22 is moved from the open position to the closed position to occlude the arch wire slot and retain the arch wire, the arch wire may be one caught in the clip; particularly between the lateral arms. In such an event, the arch wire may pass within the arch wire slot lingually of one lateral arm and pass labially over the other lateral arm. The middle arm prevents this occurrence which eliminates a cause of bracket (e.g. clip) breakage.

Additionally, in embodiment, the cut out 52 further defines the gingival tie wings 18, making these structures more prominent without enlarging these structures over similar embodiments. The increased prominence of the gingival tie wings 18 make these structures easier to use and more effective as extra ligature points for the orthodontist. This is an improvement over the art as previous self-ligating brackets have results in limited functionally of gingival tie wings 18.

In an exemplary embodiment, it will be noted that ridge surface 55 of the central ridge 54 and the lateral ledges 48 are located at a same height above the bottom of the arch wire slot 20. This is exemplarily seen in FIG. 4. Additionally, in embodiments, the lateral arms 36 and middle arm 38 extend the same distance in a gingival-occlusal dimension. This is exemplarily depicted in FIG. 2. In one exemplary embodiment, the self-ligating bracket 10 achieves an advantage over other self-ligating brackets in the art in that covered or partially covered portions of the clip 22 (e.g. lateral arms 36) received within recesses 46, can obscure the view of the orthodontist and impair visual confirmation that the clip 22 had been moved fully into the closed position. If the clip 22 is not moved fully into the closed position, the clip 22 may be less effective in retaining the arch wire (not depicted) within the arch wire slot 20. By the similarity in length of the middle arm 38 to the lateral arms 36 as well as the similarities in position between the lateral ledges 48 and the central ridge 54, a position of the middle arm 38 provides an accurate indication of the relative positions of the lateral arms 36. Therefore, alignment of the middle arm 38 into a fully closed position relative to the central ridge 54 and cut out 52 provides the orthodontist with a visual confirmation that the clip 22 is in the fully closed configuration.

Additionally, when the clip 22 is in the closed position wall 56, and in some embodiments, the ridge extension 57, extend into respective cut outs 58 between the lateral arms 36 and the middle arm 38. This additionally promotes alignment of the lateral arms 36 and middle arm 38 into engagement with the respective lateral ledges 48 and ridge surface 55 of the central ridge 54, and also further restrains movement of the clip 22 in the mesial-distal direction. In the embodiment depicted, the clip 22 is restrained from movement in the mesial direction by at least engagement of the distal arm with the wall 598 of the distal recess and the middle arm 38 with the mesial ridge extension 57. The clip 22 may be restrained from movement in the distal direction by at least engagement of the mesial arm 36 with the wall 56 of the mesial recess 46 and the middle arm 38 with the distal ridge extension 57.

Embodiments of the self-ligating bracket 10 further include an alignment mark 60 which can exemplarily be a groove in the base 12, but may also be another form of visual indicator, including a two dimensional indicator or one that is denoted by color. The alignment mark 60 further provides a visual guide to an orthodontist when the orthodontist places the bracket 10 on the tooth of the patient.

Figure 5:
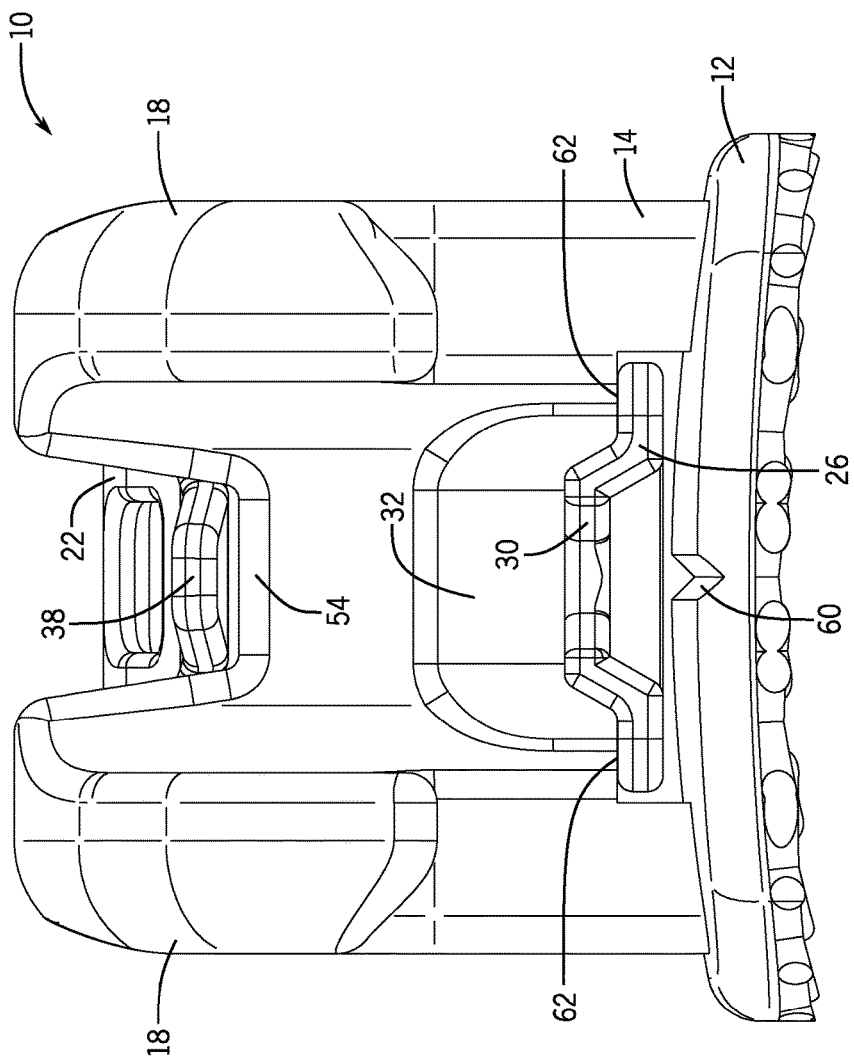
FIG. 5 is a rear view of the exemplary embodiment of the self-ligating bracket.
Figure 6:
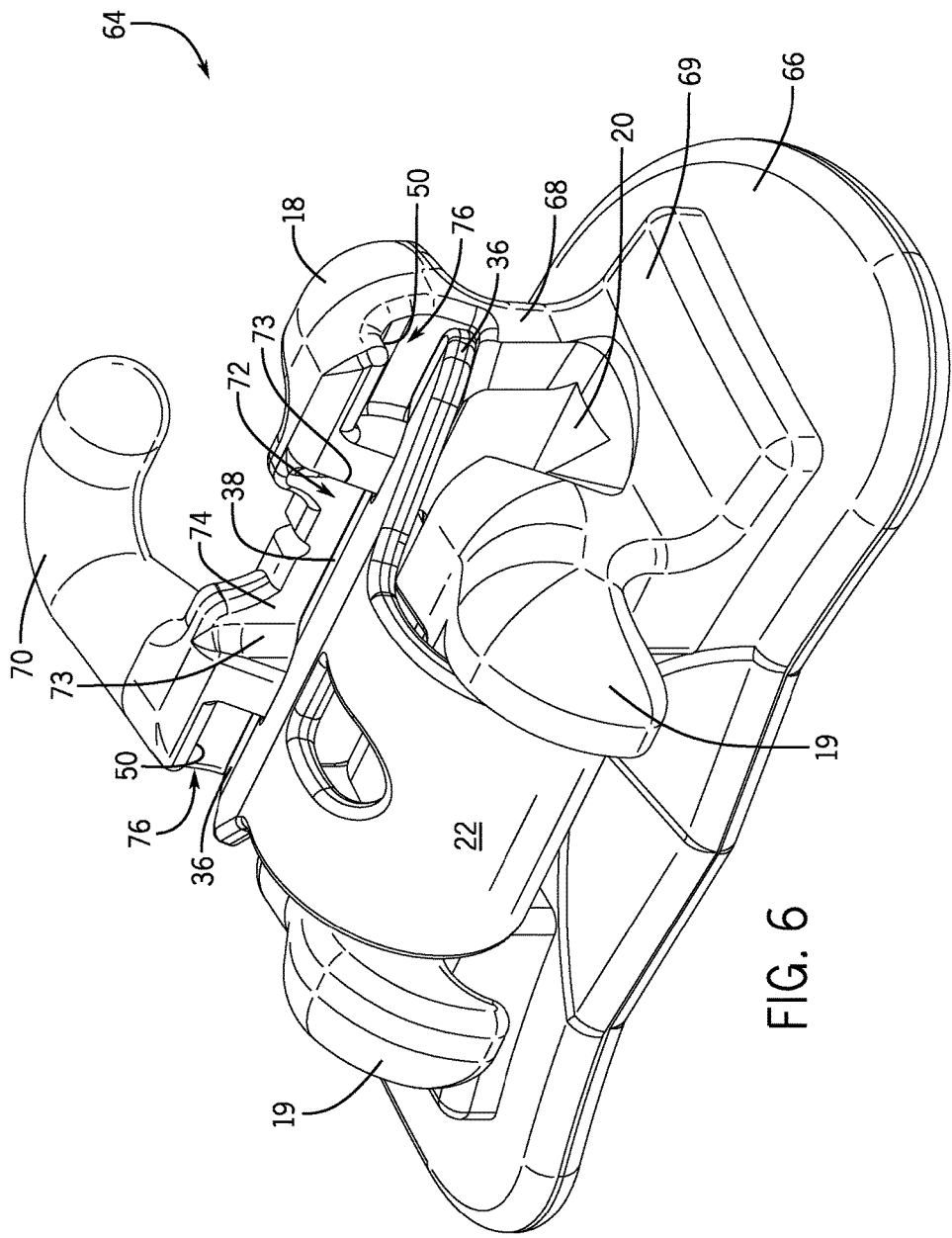
FIG. 6 is a perspective view of an exemplary additional embodiment of a self-ligating bracket.

As can best be seen in FIG. 5, in embodiments, the bracket body 14, further includes lips 62 which respectively engage the labial surface of the lower arm 26 at the mesial and distal edges of the lower arm 26. These lips 62 further promote alignment of the lower arm 26 and maintain the lower arm 26 in a predetermined position, particularly when the clip 22 is in the closed configuration. The lips 62 further retain the lower arm 26 in a position relative to the bracket body 14, between the bracket body 14 and the pad 12, which promotes consistency in the positive engagement force applied by the upper arm 24.

Embodiments of the self-ligating bracket 10 as disclosed herein may be arranged in active and/or passive arrangements. In an active self-ligating arrangement while the clip 22, and more specifically lateral arms 36 and middle arm 38 as well as the ledges 48 and central ridge 54 are dimensioned to resiliently engage when the clip 22 is in the closed position, when an arch wire is positioned within the arch wire slot 20, at least one of the lateral arms 36 and middle arm 38 resiliently engage the arch wire instead. In embodiments, this may be due to the dimensions of at least one of the arch wire and the arch wire slot 20, ledges 48, and central ridge 54. For example, in an embodiment, the self-ligating bracket may actively engage the arch wire with any arch wire dimensions. If the dimension of the arch wire, particularly in a lingual-labial dimension, is greater than a distance between a floor of the arch wire slot 20 and the lateral ledges 48 and/or central ridge 54, the clip 22 will actively engage the arch wire. If the dimensions of the arch wire is less than a distance between the floor of the arch wire slot and the lateral ledges 48 and/or central ridge 54, engage the lateral ledges 48 and/or central ridge 54 in a passive ligation arrangement. In a still further embodiment, a plurality of arch wires are available to an orthodontist to select from to progress (e.g. circular or rectangular) and may have different cross-section dimensions (e.g. 0.018 or 0.022). In an embodiment, the arch wire slot 22, the lateral ledges 48 and the central ridge 54 may be arranged and/or dimensioned such that the clip 22 passively ligates a 0.018 arch wire while the clip actively ligates a 0.022 arch wire.

FIGS. 6-10 depict an additional exemplary embodiment of a self-ligating bracket 64. The self-ligating bracket 64 is exemplarily configured as a single convertible buccal tube configured to be secured to a molar of the patient. In the embodiment depicted, the self-ligating bracket 64 includes a bracket body 68 secured to a bonding pad 66 which is configured to be secured to the tooth of the patient. However, it will be recognized that in alternative embodiments, a bonding pad 66 is not used and rather the bracket body 68 is secured to a molar band (not depicted). Flanges 69 on the bracket body 68 may facilitate securement to either a boding pad 66 or a molar band, for example by welding. It will be recognized that like reference numerals are used herein in order to identify generally similar structures between embodiments for the purpose of conciseness. It will also be recognized that various combinations of disclosed and/or depicted features between the embodiments may be used in additional embodiments while remaining within the scope of the present disclosure although such embodiments are not explicitly depicted in the Figures.

It will also be noted that the embodiment of the self-ligating bracket 64 further includes a hook 70. In use, orthodontists may use the hook 70 as an additional ligature point, exemplarily to connect two or more brackets together.

Figure 7:
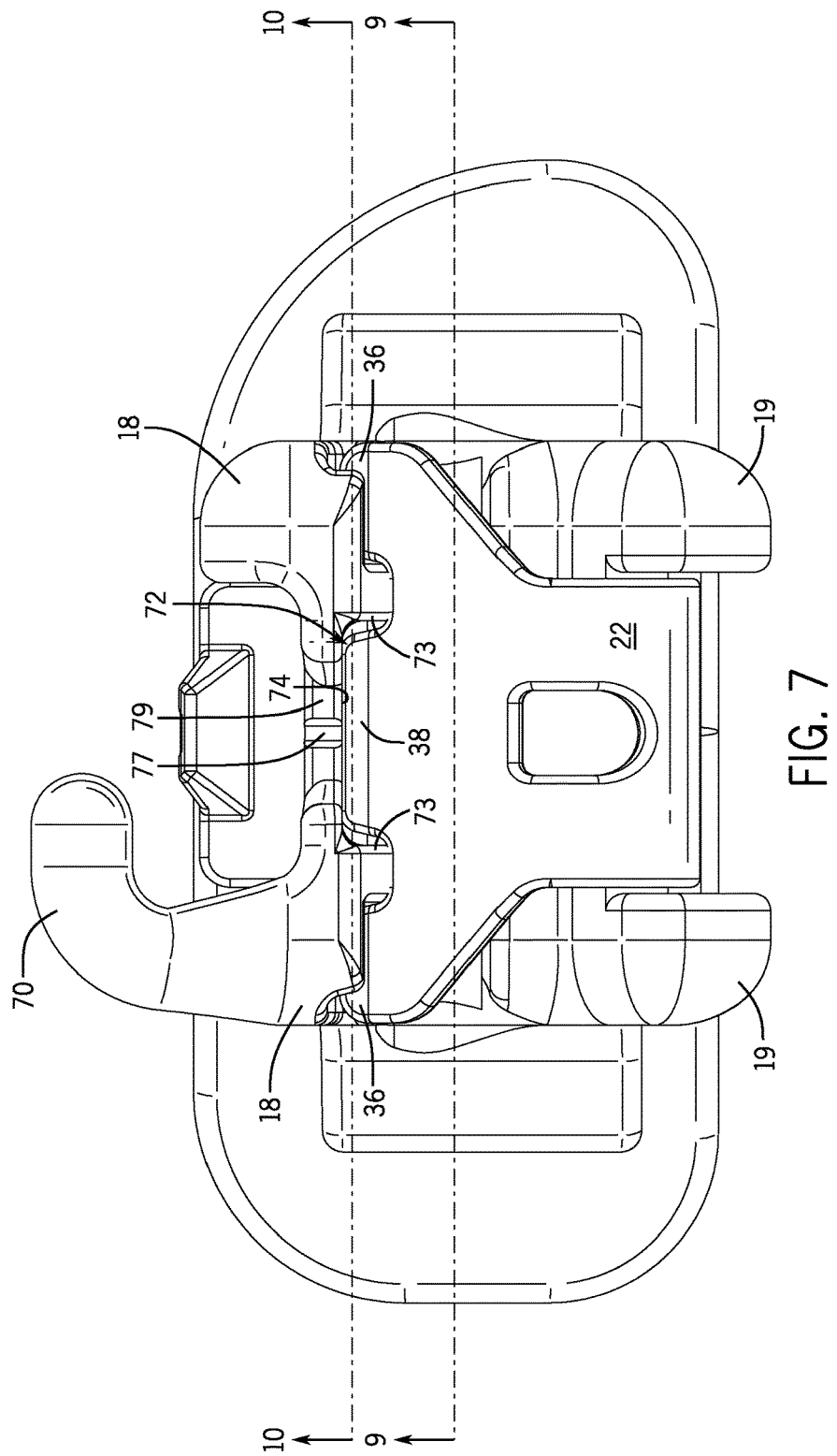
FIG. 7 is a top view of the exemplary additional embodiment of the self-ligating bracket.

As best seen in FIG. 7, the exemplary embodiment of the self-ligating bracket 64 includes a cut out 72 between the tie wings 18 which does not extend all the way through the bracket body 68, but rather defines an end wall 74 and side walls 73 in the bracket body. These features exemplarily provide an additional visual cue as to the relative position between the middle arm 38 and the end wall 74 such that the orthodontists can visually confirm that the clip 22 is in the closed configuration. The cut out 72 further extends in the labial-lingual dimension until a ridge surface 75 of a central ridge 80 between the tie wings 18. In embodiments, the middle arm 36 engages the ridge surface 75 when the clip 22 is in the closed position. In an additional embodiment, an alignment mark 77 is located on a bracket body portion 79 between the tie wings 18 that remains from cut out 72. The alignment mark 77 is therefore located in the bracket body at a position labially of the middle arm 38, yet may be recessed relative to a labial surface of the gingival tie wings 18 and thus be located lingually of the labial surface of the gingival tie wings 18.

Figure 8:
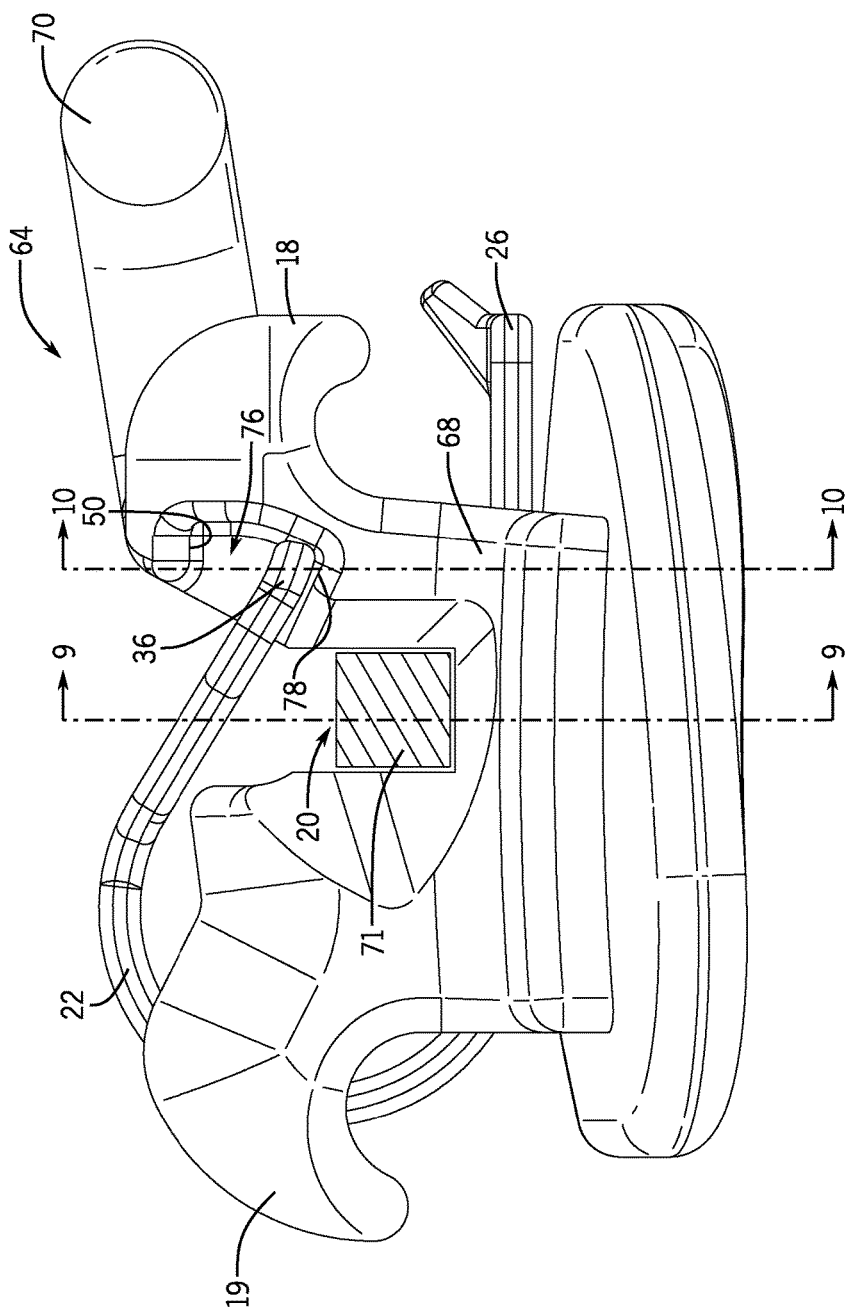
FIG. 8 is a side view of the exemplary additional embodiment of the self-ligating bracket.
Figure 9:
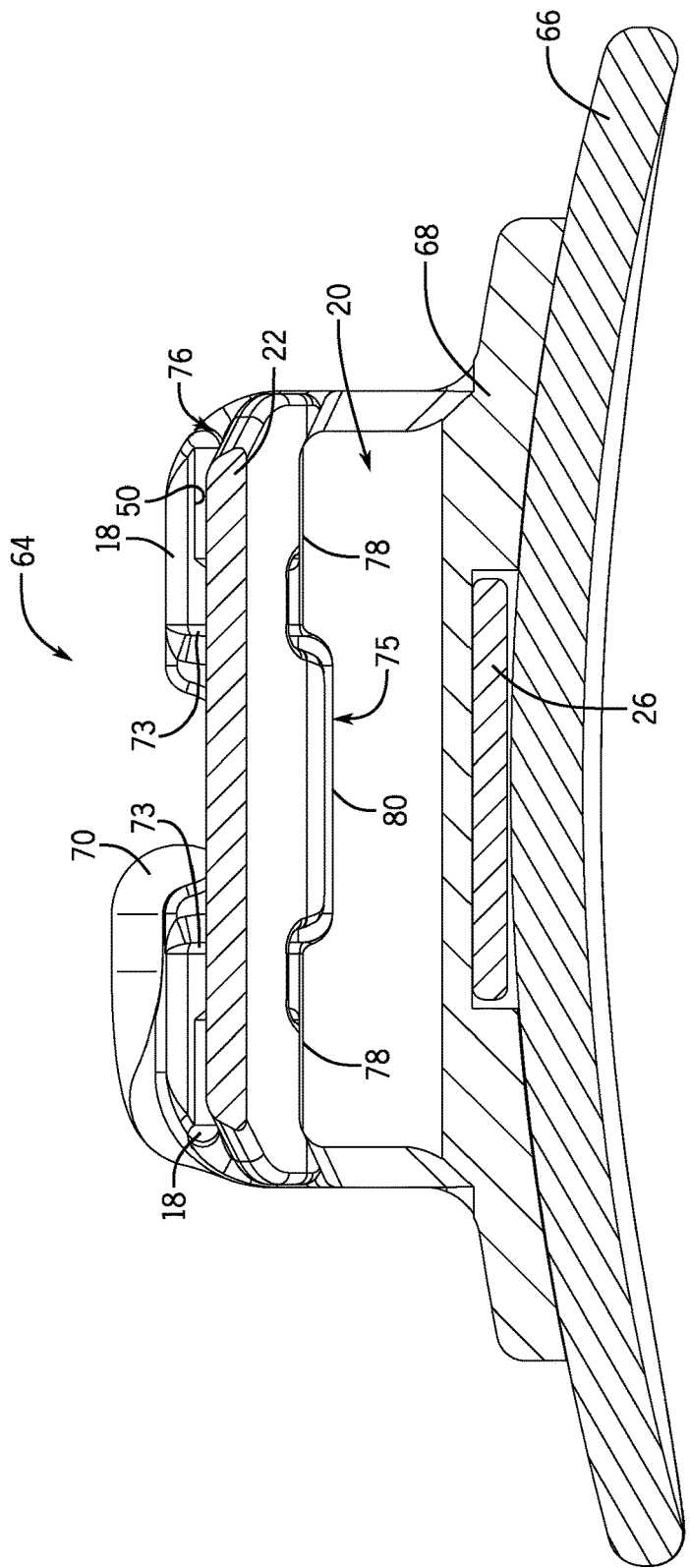
FIG. 9 is a front sectional view taken along line 9-9 of FIGS. 7 and 8.
Figure 10:
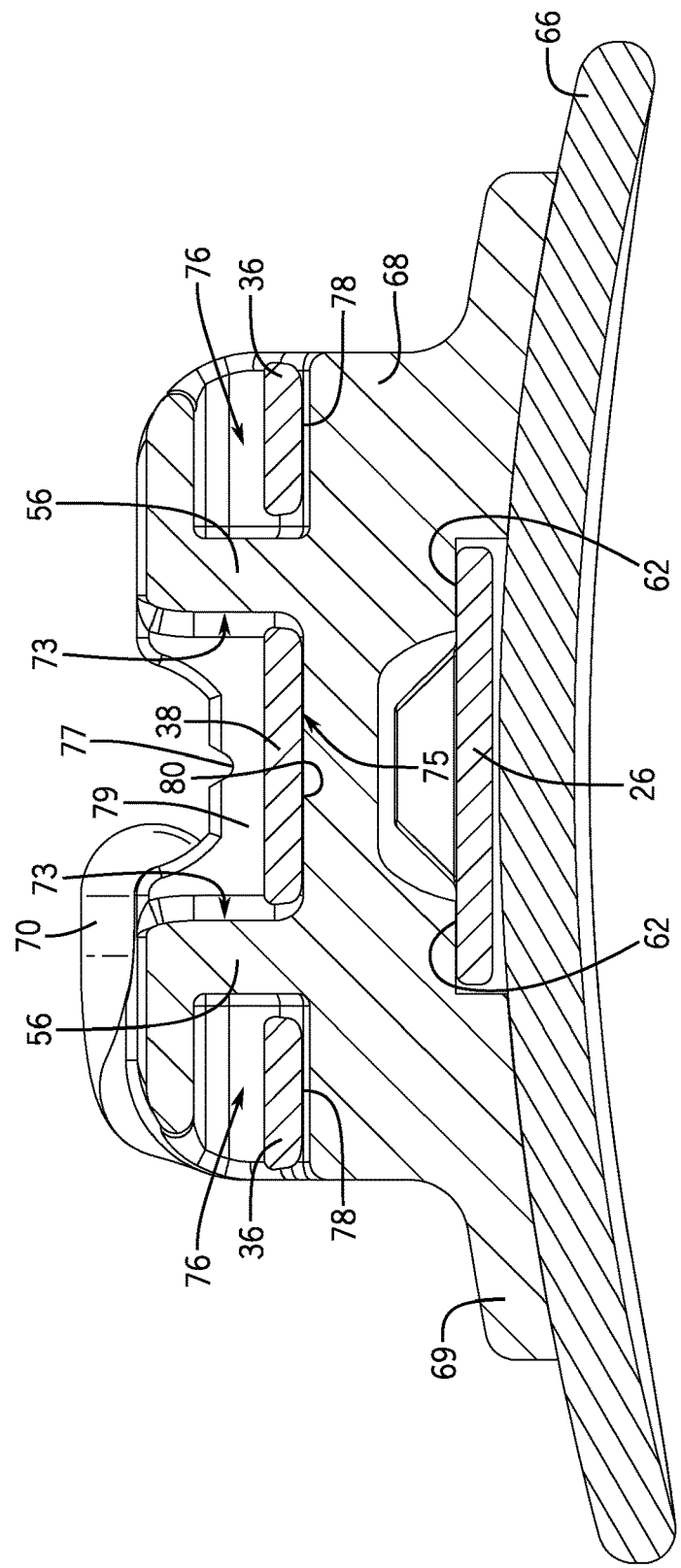
FIG. 10 is a front sectional view taken along line 10-10 of FIGS. 7 and 8.
Figure 11:
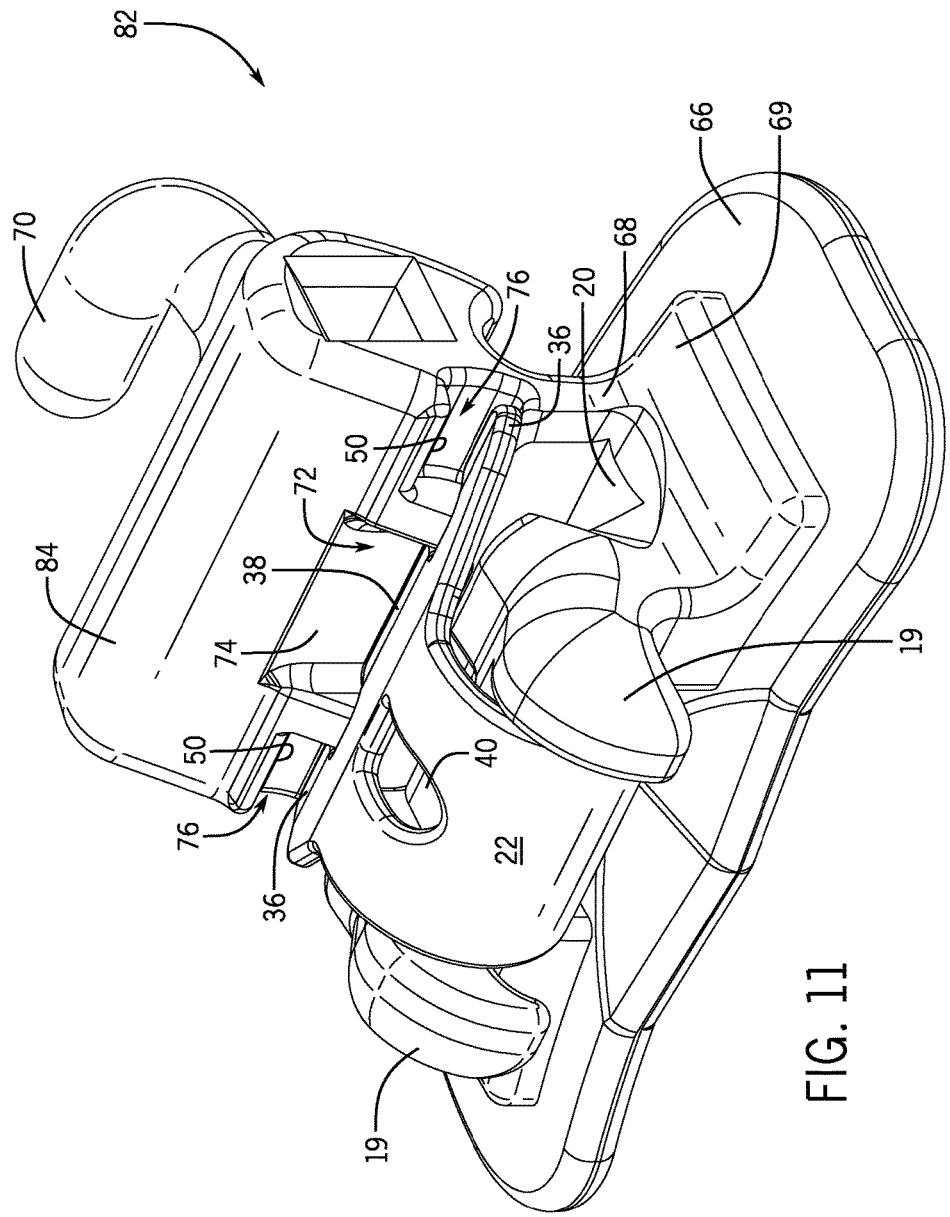
FIG. 11 is a front perspective view of an exemplary further embodiment of a self-ligating bracket.
Figure 12:
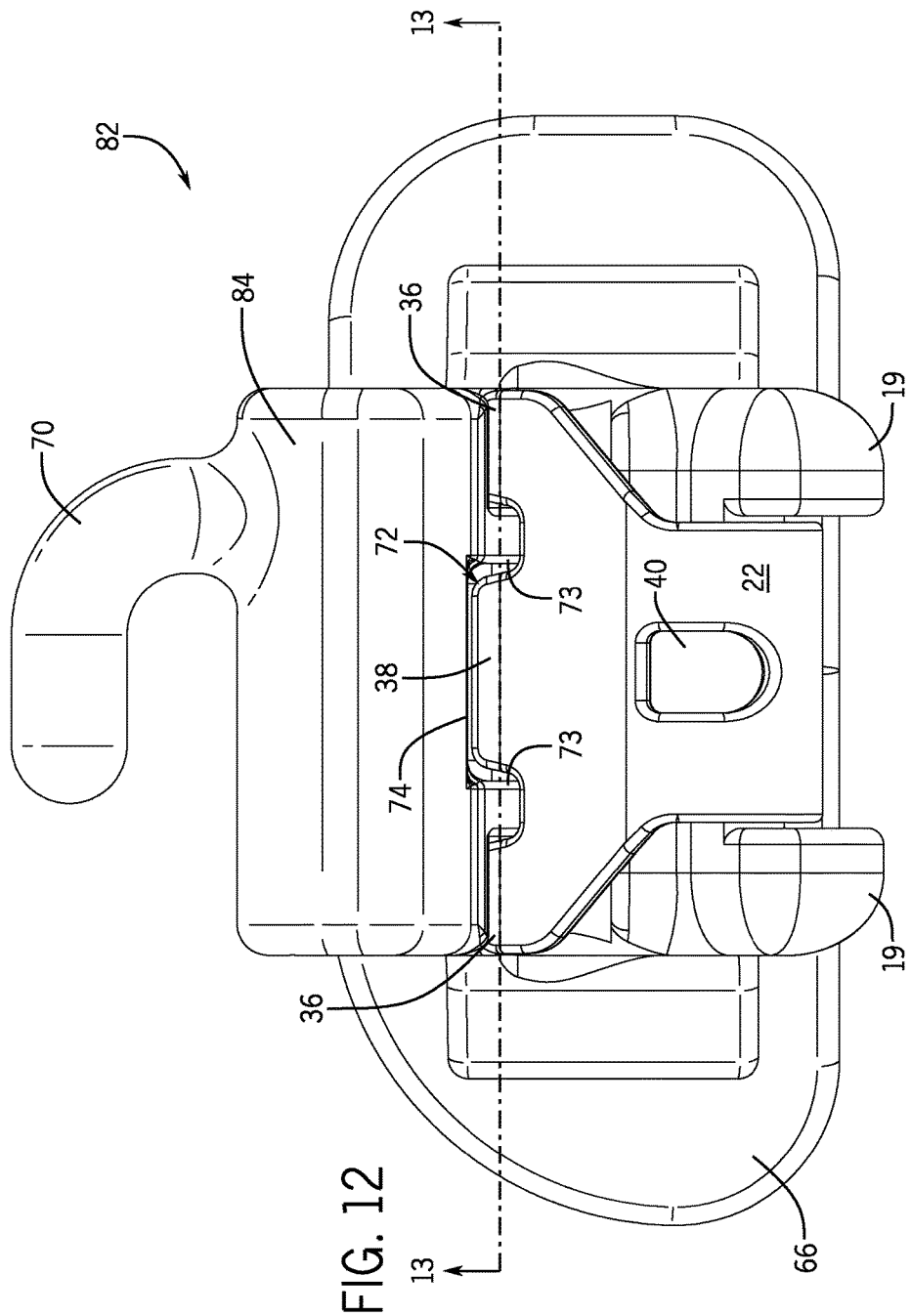
FIG. 12 is a top view of the exemplary further embodiment of the self-ligating bracket.

Additionally, as can be best seen in FIG. 8, the recesses 76 located in the tie wing 18 and configured to receive the lateral arms 36 are arranged such that the lateral ledge 78 extends at an angle in the buccal-lingual dimension, particularly as compared to the lateral ledge 48 as depicted in FIGS. 1-5. FIG. 8 further depicts an arch wire 71 in cross section and positioned within the arch wire slot 20. The arch wire 71 is exemplarily passively ligated as the lateral arms 36 and middle arm 38 do not engage the arch wire 71 when the clip 22 is in the closed position and the arch wire 71 is not otherwise forced into contact within the clip. As seen in FIG. 9, the points at which the lateral ledges 78 begin from the arch wire slot 20, the lateral ledges 78 are at a higher position in the buccal-lingual dimension than the central ridge 80. However, as can be seen in FIG. 10 at the respective ends of the lateral arms 36 and middle arm 38, the lateral ledges 78 are at a same relative height as the central ridge 80. In an embodiment, a correspondence between an angle of the lateral edge 78 surface and the lateral arms 36 results in an increased engagement surface area therebetween which promotes retention of the lateral arms 36 in the recess 76.

Figure 13:
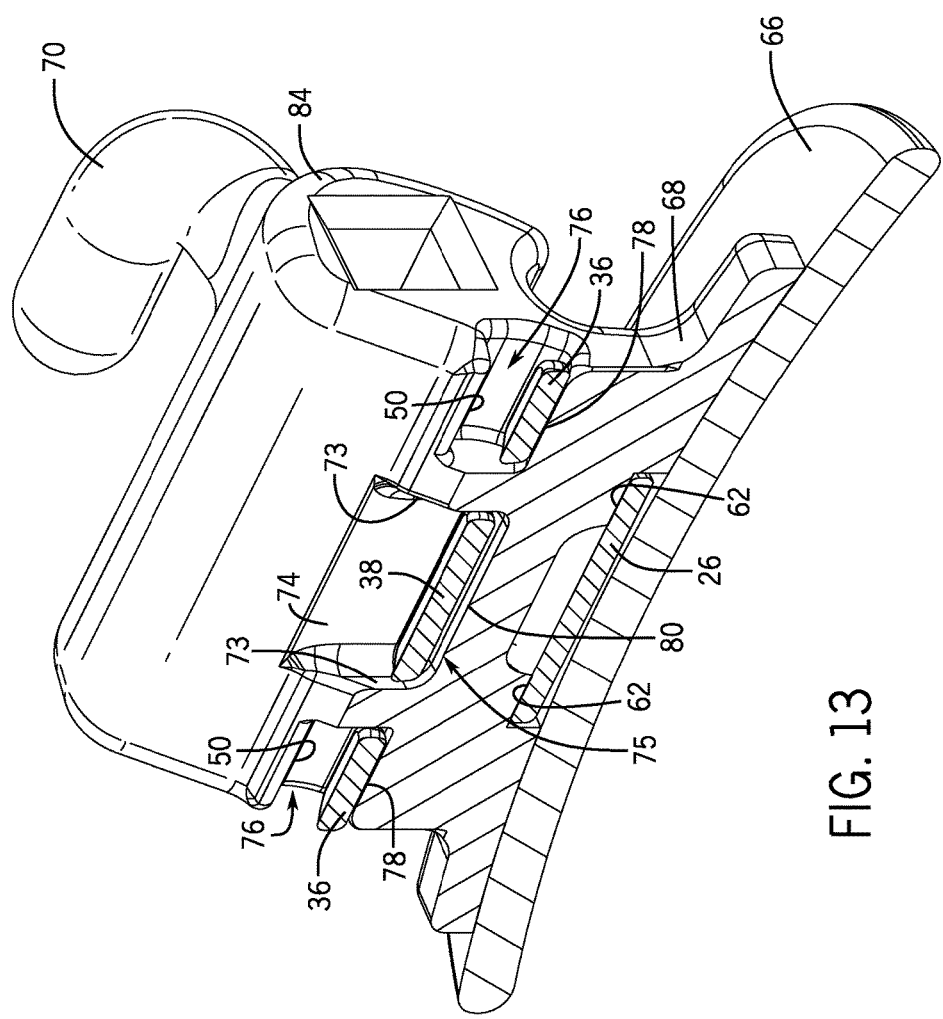
FIG. 13 is a front perspective sectional view taken along line 13-13 of FIG. 12.
Figure 14:
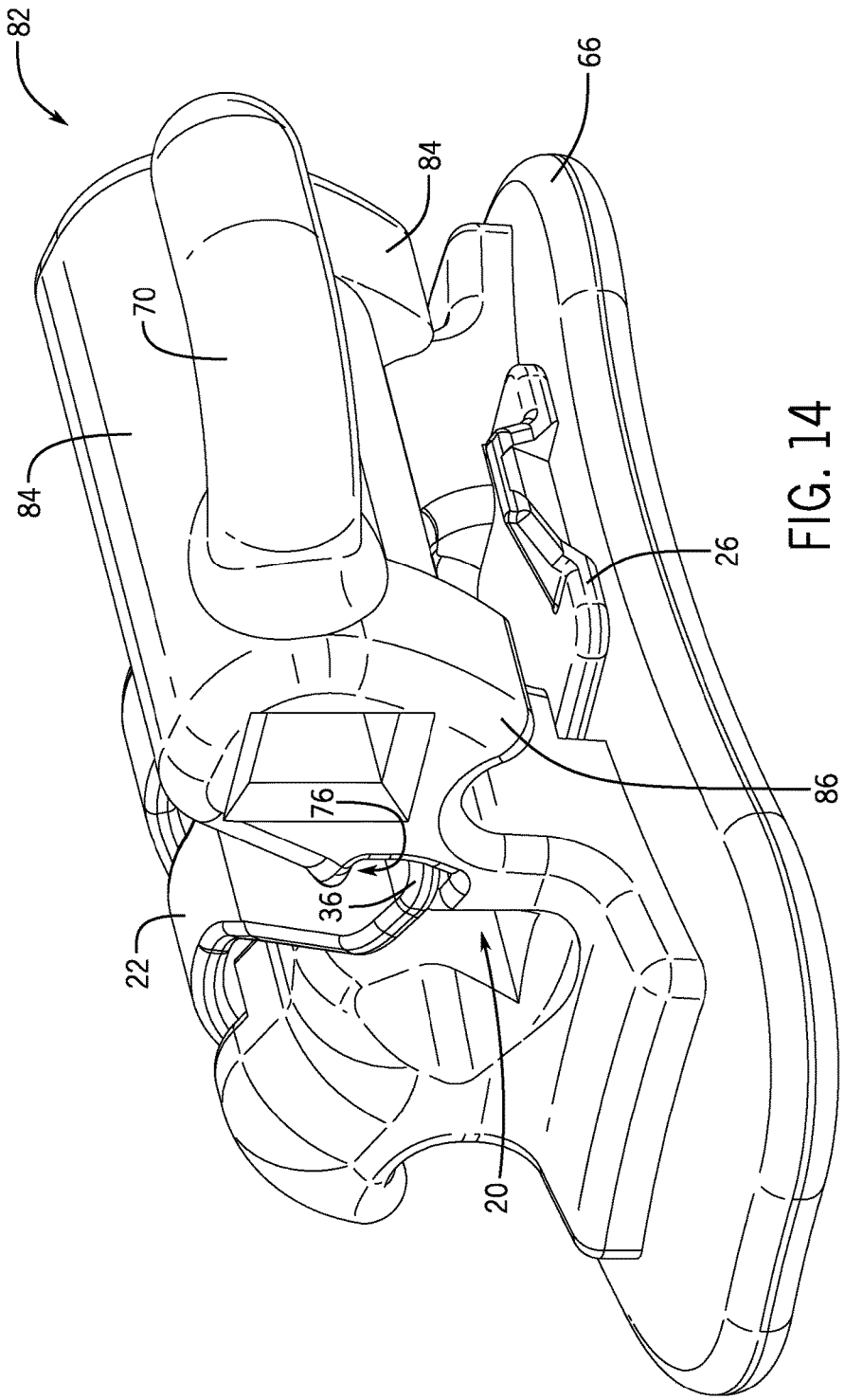
FIG. 14 is a rear perspective view of the exemplary further embodiment of the self-ligating bracket.

FIGS. 11-14 depict a still further exemplary embodiment of a self-ligating bracket 82. The self-ligating bracket 82 is exemplarily a convertible double molar tube configuration in which a secondary tube 84 is secured to the bracket body 68. In the embodiment of the self-ligating bracket 82 depicted, a hook 70 further extends from the secondary tube 84. In the embodiment depicted, the secondary tube 84 effectively replaces the individual tie wings 18 comparatively depicted in FIGS. 1-5, yet may include tie wings 86 which extend from the buccal tube 84. As can be seen in FIGS. 11-14, the cut out 72 exemplary extends into the buccal tube 84, rather than explicitly between the tie wings as depicted in other embodiments. FIG. 13 exemplary depicts the relationship between the lateral ledges 78 and the central ridge 80 and thereby the lateral arm 36 and the middle arm 38 as previously described is further maintained in this exemplary additional embodiment.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A self-ligating bracket, comprising:
a bracket body with an arch wire slot defined therethrough in a mesial-distal dimension, the bracket body comprising:
a mesial recess having a first lateral ledge located at a mesial side of the bracket body and extending into the bracket body from the arch wire slot, a distal recess having a second lateral ledge located at a distal side of the bracket body and extending into the bracket body from the arch wire slot, and a central ridge defining a ridge surface, the ridge surface separated from the lateral ledges respectively by mesial and distal walls; and
a clip comprising a first arm and a second arm, the first arm and second arm connected by a U-shaped portion, and the first arm terminates in a mesial arm, a distal arm, and a middle arm between the mesial arm and the distal arm, the middle arm separated from the mesial arm by a first cut out and the middle arm separated from the distal arm by a second cut out, the clip moveable between an open position wherein the arch wire slot is accessible and a closed position wherein the arch wire slot is occluded by at least a portion of the mesial arm, the distal arm, and the middle arm, wherein in the closed position, the mesial arm engages the first lateral ledge in the mesial recess, the distal arm engages the second lateral ledge in the distal recess, and the middle arm engages the ridge surface.

2. The self-ligating bracket of claim 1, wherein the clip further comprises a transition portion that connects the U-shaped portion to the distal arm, the mesial arm, and the middle arm, and when the clip is in the closed position, at least a portion of the transition portion occludes the arch wire slot.

3. The self-ligating bracket of claim 2, wherein the U-shaped portion has a first width in the mesial-distal dimension and the clip has a second width in the mesial-distal dimension between the mesial arm and the distal arm and the second width is greater than the first width.

4. The self-ligating bracket of claim 1, wherein a distal edge of the distal arm is coextensive with a distal side of the bracket body and a mesial edge of the mesial arm is coextensive with a mesial side of the bracket body.

5. The self-ligating bracket of claim 1, further comprising:
a gap defined in the bracket body, the second arm of the clip translatably movable within the gap;
a ridge extending from an end of the second arm;
a ridge stop defined in the bracket body and adapted to engage the ridge to at least partially define the open position of the clip; and
first and second lips extending from the ridge stop, the first and second lips engage the second arm to slidably retain the second arm.

6. The self-ligating bracket of claim 1, wherein the lateral ledges and the ridge surface of the central ridge are spaced a same height above a bottom of the arch wire slot.

7. The self-ligating bracket of claim 1, wherein the lateral ledges and the ridge surface of the central ridge terminate at a same position in a gingival direction from the arch wire slot.

8. The self-ligating bracket of claim 7, wherein the mesial arm, the distal arm, and the middle arm all extend the same distance in the gingival dimension.

9. The self-ligating bracket of claim 7, wherein an alignment of the middle arm with the central ridge when the clip is in the closed position provides visual confirmation that the mesial arm and the distal arm are in the closed position.

10. The self-ligating bracket of claim 1, wherein the mesial recess further comprises a first ceiling and the distal recess further comprises a second ceiling, the first lateral ledge and the first ceiling define a range of motion for the mesial arm when the clip is in the closed position, and the second lateral ledge and the second ceiling define a range of motion for the distal arm when the clip is in the closed position.

11. A self-ligating bracket, comprising:
a bracket body comprising an arch wire slot defined therethrough in a mesial-distal dimension, the bracket body comprising a distal gingival tie wing and a mesial gingival tie wing extending gingivally of the bracket body and respectively located at mesial and distal sides of the bracket body, a mesial recess having a first lateral ledge, a first ceiling, and a mesial wall defined into the mesial gingival tie wing from the arch wire slot and a distal recess having a second lateral ledge, a second ceiling, and a distal wall defined into the distal gingival tie wing from the arch wire slot, and a cut out between the gingival tie wings defines a central ridge with a ridge surface, the ridge surface separated from the lateral ledges respectively by the mesial and distal walls; and
a clip comprising a labial arm and a lingual arm, the labial arm and the lingual arm connected by a U-shaped portion, and the labial arm terminates in a mesial arm, a distal arm, and a middle arm between the mesial arm and the distal arm, the middle arm separated from the mesial arm by a first cut out and the middle arm separated from the distal arm by a second cut out, the clip moveable between an open position wherein the arch wire slot is accessible and a closed position wherein the arch wire slot is occluded by at least a portion of the mesial arm, the distal arm, and the middle arm, wherein the clip is adapted such that when in the closed position, the mesial arm engages the first lateral ledge in the mesial recess, the distal arm engages the second lateral ledge in the distal recess, and the middle arm engages the ridge surface.

12. The self-ligating bracket of claim 11, wherein the lateral ledges and the ridge surface of the central ridge terminate at a same position in a gingival direction from the arch wire slot.

13. The self-ligating bracket of claim 12, wherein a distal edge of the distal arm is coextensive with a distal side of the bracket body, a mesial edge of the mesial arm is coextensive with a mesial side of the bracket body, and the distal arm, mesial arm, and mesial arm extend the same distance in a gingival-occlusal dimension.

14. The self-ligating bracket of claim 12 further comprising an end wall that extends between the mesial and distal gingival tie wings and further defines a gingival end of the ridge surface of the central ridge.

15. The self-ligating bracket of claim 11, wherein the first lateral ledge and the second lateral ledge are angled in the lingual direction and the gingival direction, and at least a portion of the mesial arm of the clip and the distal arm of the clip respectively corresponding to the first lateral ledge and the second lateral ledge when the clip is in the closed position.

16. An orthodontic treatment system comprising:
a plurality of self-ligating brackets, each self-ligating bracket of the plurality comprising:
a bracket body with an arch wire slot defined therethrough in a mesial-distal dimension, the bracket body comprising a mesial recess having a first lateral ledge located at a mesial side of the bracket body and extending into the bracket body from the arch wire slot, a distal recess having a second lateral ledge located at a distal side of the bracket body and extending into the bracket body from the arch wire slot, and a central ridge defining a ridge surface, the ridge surface separated from the lateral ledges respectively by mesial and distal walls; and
a clip comprising an upper arm and a lower arm, the upper arm and lower arm connected by a U-shaped portion, and the upper arm terminates in a mesial arm, a distal arm, and a middle arm between the mesial arm and the distal arm, the middle arm separated from the mesial arm by a first cut out and the middle arm separated from the distal arm by a second cut out, the clip moveable between an open position and a closed position, wherein the clip is adapted such that when in the closed position, the mesial arm engages the first lateral ledge in the mesial recess, the distal arm engages the second lateral ledge in the distal recess, and the middle arm engages the ridge surface; and
an arch wire positioned within the arch wire slot of each of the plurality of self-ligating brackets, wherein when the clips of the self-ligating brackets are in the open position, the arch wire slots are accessible for placement and removal of the arch wire, and when the clips of the self-ligating brackets are in the closed position, the arch wire is retained within the arch wire slots of each of the self-ligating brackets.

17. The orthodontic treatment system of claim 16, wherein the arch wire is selected from a plurality of arch wires comprising a first arch wire having a first cross-sectional area and a second arch wire having a second cross-sectional area, the first cross-sectional area being smaller than the second cross-sectional area.

18. The orthodontic treatment system of claim 17, wherein treatment is progressed by interchanging the second arch wire for the first arch wire, wherein the self-ligating brackets of the plurality of self-ligating brackets close in a passive closed position for the first arch wire and close in an active closed position for the second arch wire.

19. The orthodontic treatment of claim 17, wherein the lateral ledges and the central ridge are spaced from a bottom of the arch wire slot a distance greater than a dimension of the first arch wire.

20. The orthodontic treatment of claim 17, wherein the lateral ledges and the central ridge are spaced from a bottom of the arch wire slot a distance less than a dimension of the second arch wire.

21. A self-ligating bracket, comprising:
a bracket body with an arch wire slot defined therethrough in a mesial-distal dimension, the bracket body comprising:
a mesial recess having a first lateral ledge located at a mesial side of the bracket body and extending into the bracket body from the arch wire slot, a distal recess having a second lateral ledge located at a distal side of the bracket body and extending into the bracket body from the arch wire slot, and a central ridge defining a ridge surface, the ridge surface separated from the lateral ledges respectively by mesial and distal walls and the lateral ledges and the ridge surface of the central ridge terminate at a same position in a gingival direction from the arch wire slot; and
a clip comprising a first arm and a second arm, the first arm and second arm connected by a U-shaped portion, and the first arm terminates in a mesial arm, a distal arm, and a middle arm between the mesial arm and the distal arm, the middle arm separated from the mesial arm by a first cut out and the middle arm separated from the distal arm by a second cut out, the clip moveable between an open position wherein the arch wire slot is accessible and a closed position wherein the arch wire slot is occluded by at least a portion of the mesial arm, the distal arm, and the middle arm, wherein in the closed position, the mesial arm engages the first lateral ledge in the mesial recess, the distal arm engages the second lateral ledge in the distal recess, and the middle arm engages the ridge surface.

* * * * *